United States Patent
Tay et al.

(10) Patent No.: US 12,102,779 B2
(45) Date of Patent: Oct. 1, 2024

(54) OBTURATOR, SHEATH AND METHOD FOR USING SAME

(71) Applicant: TWO BIRDS MEDICAL PTE. LTD., Singapore (SG)

(72) Inventors: Hsien Tsung Tay, Singapore (SG); Kiang Hiong Tay, Singapore (SG); Chin Cheung Andrew Lau, Singapore (SG); Thien Khanh Nguyen, Ho Chi Minh (VN)

(73) Assignee: TWO BIRDS MEDICAL PTE. LTD., Singapore (SG)

( * ) Notice: Subject to any disclaimer, the term of this patent is extended or adjusted under 35 U.S.C. 154(b) by 774 days.

(21) Appl. No.: 16/652,328

(22) PCT Filed: Sep. 28, 2018

(86) PCT No.: PCT/SG2018/050494
§ 371 (c)(1),
(2) Date: Mar. 30, 2020

(87) PCT Pub. No.: WO2019/066728
PCT Pub. Date: Apr. 4, 2019

(65) Prior Publication Data
US 2020/0282187 A1    Sep. 10, 2020

Related U.S. Application Data

(60) Provisional application No. 62/566,352, filed on Sep. 30, 2017.

(51) Int. Cl.
*A61M 25/09*    (2006.01)
*A61B 17/34*    (2006.01)
(Continued)

(52) U.S. Cl.
CPC .......... *A61M 25/09041* (2013.01); *A61B 17/3421* (2013.01); *A61M 25/007* (2013.01); *A61M 25/0108* (2013.01); *A61M 2025/0188* (2013.01)

(58) Field of Classification Search
CPC .......... A61M 25/09041; A61M 25/007; A61M 25/0108; A61M 25/0015;
(Continued)

(56) References Cited

U.S. PATENT DOCUMENTS

| 4,769,005 A | 9/1988 | Ginsburg et al. |
| 4,774,949 A | 10/1988 | Fogarty |

(Continued)

FOREIGN PATENT DOCUMENTS

| CN | 101513357 A | 8/2009 |
| EP | 3034125 A1 | 6/2016 |

(Continued)

OTHER PUBLICATIONS

International Search Report issued in connection with International Application No. PCT/SG2018/050494 on Nov. 27, 2018.
(Continued)

*Primary Examiner* — Robert J Utama
*Assistant Examiner* — Justin L Zamory
(74) *Attorney, Agent, or Firm* — Potomac Law Group, PLLC; John J. Penny, Jr.

(57) ABSTRACT

An obturator comprising a hollow distal end portion, the distal end portion comprising a distal end and a side hole located proximally of the distal end, the side hole being for receipt of a guidewire and to direct the guidewire laterally from the obturator.

10 Claims, 7 Drawing Sheets

(51) Int. Cl.
*A61M 25/00* (2006.01)
*A61M 25/01* (2006.01)

(58) Field of Classification Search
CPC .............. A61M 2025/0188; A61M 2025/0008; A61M 2025/0004; A61B 17/3421; A61B 2017/3435; A61B 17/0469
See application file for complete search history.

(56) References Cited

U.S. PATENT DOCUMENTS

| | | | |
|---|---|---|---|
| 5,137,517 A * | 8/1992 | Loney | A61M 25/09041 |
| | | | 606/1 |
| 5,250,029 A * | 10/1993 | Lin | A61M 25/1011 |
| | | | 606/192 |
| 6,217,527 B1 | 4/2001 | Selmon et al. | |
| 9,199,064 B2 | 12/2015 | Morero | |
| 2003/0036768 A1 | 2/2003 | Hutchins et al. | |
| 2003/0045836 A1 | 3/2003 | Batiste | |
| 2003/0158521 A1 * | 8/2003 | Ameri | A61B 17/3496 |
| | | | 604/117 |
| 2005/0075647 A1 | 4/2005 | Walters et al. | |
| 2008/0082080 A1 * | 4/2008 | Braga | A61M 25/0069 |
| | | | 604/523 |
| 2009/0088790 A1 * | 4/2009 | Parodi | A61F 2/958 |
| | | | 606/200 |
| 2014/0276762 A1 | 9/2014 | Parsonage | |

FOREIGN PATENT DOCUMENTS

| | | |
|---|---|---|
| JP | 2001137350 A | 5/2001 |
| JP | 2002525163 A | 8/2002 |
| JP | 2003526481 A | 9/2003 |
| JP | 2015036051 A | 2/2015 |
| JP | 2017113209 A | 6/2017 |
| JP | 2020535936 A | 12/2020 |
| WO | 0018323 A2 | 4/2000 |
| WO | 0168177 A1 | 9/2001 |

OTHER PUBLICATIONS

Office Action for Japanese Patent Application No. 2020-539672 issued on Feb. 13, 2023 (includes English language translation).

* cited by examiner

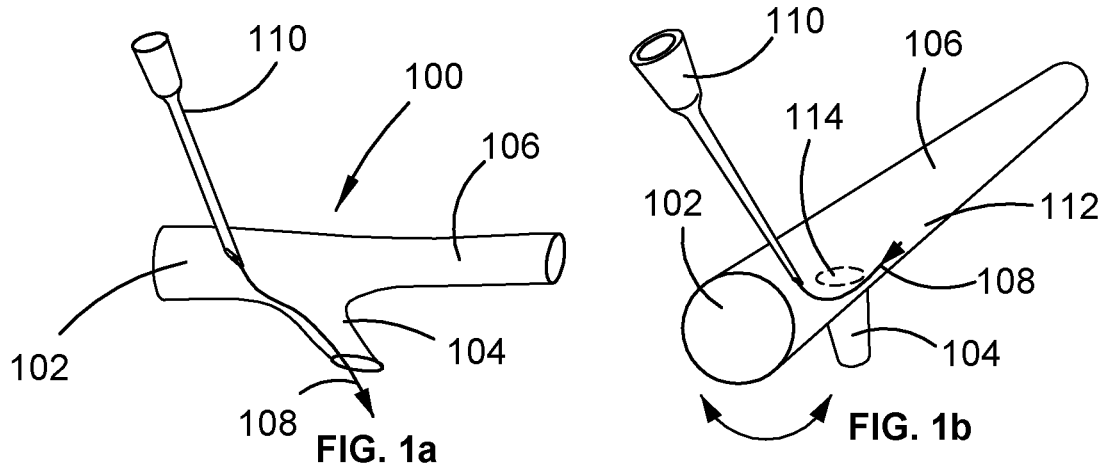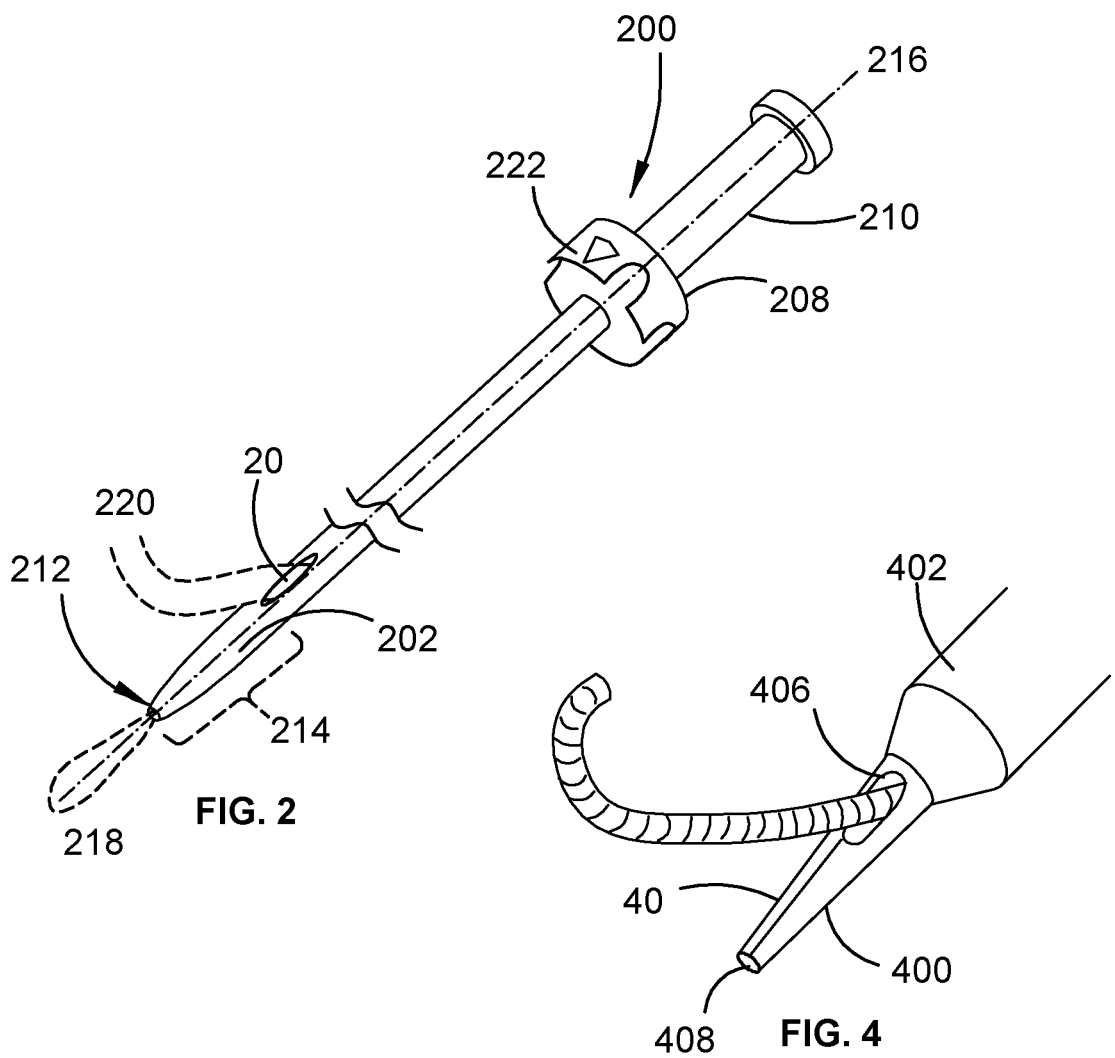

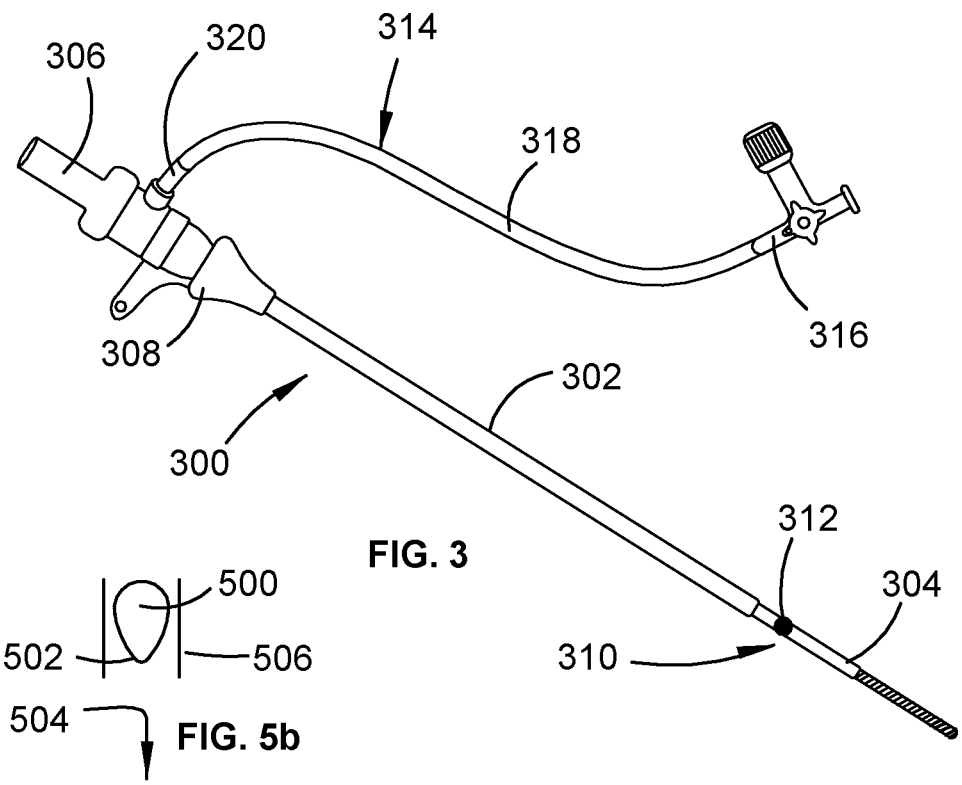
FIG. 3
FIG. 5a
FIG. 5b
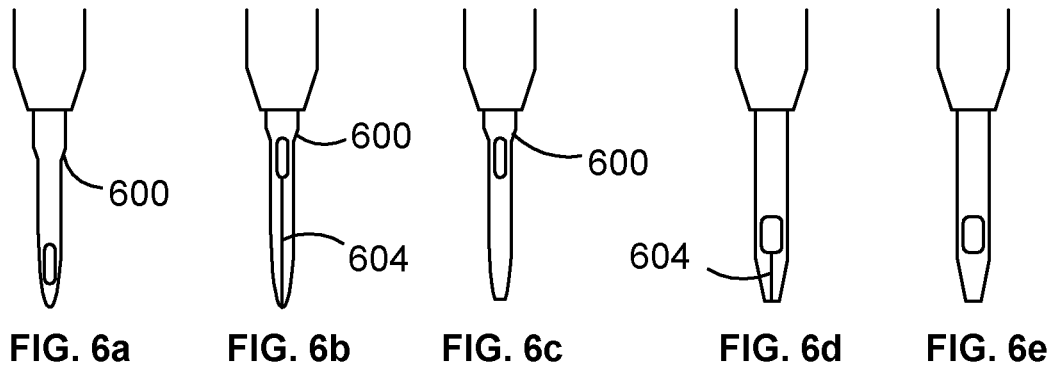
FIG. 6a  FIG. 6b  FIG. 6c  FIG. 6d  FIG. 6e
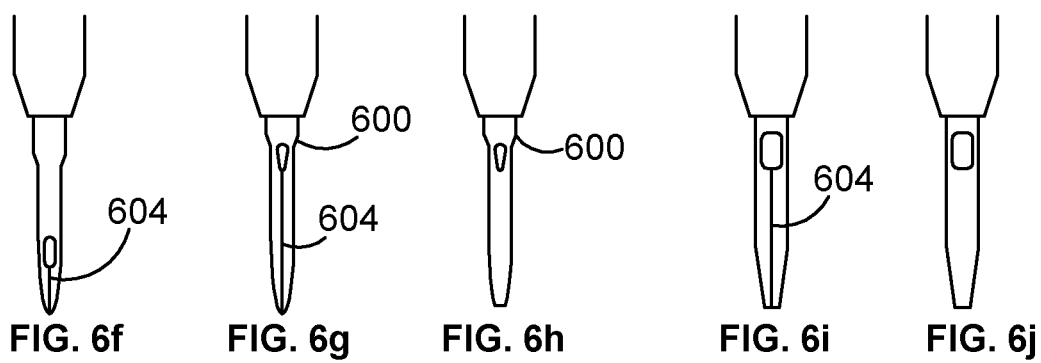
FIG. 6f  FIG. 6g  FIG. 6h  FIG. 6i  FIG. 6j

OBTURATOR, SHEATH AND METHOD FOR USING SAME

The present application claims priority under 35 U.S.C. § 119 to U.S. Provisional Patent Application No. 62/566,352 filed on Sep. 30, 2017, and under 35 U.S.C. § 365 to International Application No. PCT/SG2018/050494 filed on Sep. 28, 2018. The entire contents of these applications are incorporated herein by reference in their entirety.

TECHNICAL FIELD

The present disclosure relates to an obturator, a cannula assembly, and methods for positioning or repositioning a guidewire and cannula.

BACKGROUND

Modern medical techniques generally need to balance the comfort of the patient with the time taken to perform procedures, the expense of those procedures and the associated risks. If an error is made during a procedure, it is desirable to rectify the error with as little deviation from the correct procedure as possible, and without increasing risk— e.g. without having to perform multiple penetrations of the subject's skin.

Antegrade peripheral revascularization, for example, can require guidewire access to the superficial femoral artery via needle-puncture into the common femoral artery (CFA). The CFA is often the site of choice as the femoral head is beneath and it facilitates effective post-procedure compression for haemostasis and prevention of external bleeding, retroperitoneal haemorrhage and pseudo-aneurysm formation.

The initial needle puncture is usually done blind by palpation alone, under fluoroscopy or else with the aid of ultrasound visualization. This is followed by insertion of the guidewire which is also typically blind, followed by insertion of an access sheath over the guidewire by the Seldinger technique.

The deep formal artery—profunda femoris artery (PFA)—can be accidentally cannulated instead of the superficial femoral artery (SFA). This may be due to procedural or anatomical factors.

Procedurally, guidewire-insertion is done blind as it requires a bimanual approach and many operators do not ultrasound or perform fluoroscopy during this step. This means the guidewire will take whichever initial trajectory it has upon exiting the needle. Moreover, interaction with pre-existing stenotic disease may skew the direction of the guidewire.

Anatomically, the real-estate for puncture of the CFA can be very short (about 1-1.5 cm) and the PFA (deep femoral artery) ostium tends to be situated on the lower surface of the artery resulting in preferential passage of the needle-directed guidewire into it (see FIG. 1). This can be problematic since SFA access must be achieved before revascularization can take place. Salvage of the guidewire and correction of its trajectory into the SFA extends the time taken for the operative duration, and increases the volume of radiation exposure and contrast used. Moreover, repeated rewiring may also injure or dissect the PFA.

Not infrequently, access is lost and a second puncture needs to be made. Repuncture carries the additional risks of bleeding, hematoma and pseudo-aneurysm formation.

Techniques to prevent PFA cannulation centre around puncturing more proximally on the CFA with the intention to "bounce" the wire off the back-wall into the SFA. Such techniques can often be ineffective. Moreover, the vasculature includes high bifurcations, making such high puncture techniques dangerous. For example, puncturing above the inguinal ligament can result in occult retroperitoneal haemorrhage which is potentially life-threatening. Calcific plaques on the front wall may also deflect the expected path of the guidewire into the PFA. Not infrequently the guidewire snakes along the back wall instead of bouncing off it.

Salvaging a PFA cannulation involves tentative withdrawal of the sheath, and guidewire, out of the PFA into the CFA and attempting to re-advance the guidewire down the SFA under angiographic guidance. The sheath then follows over the guidewire once access has been secured. During this time the access is most at risk as the sheath can come back out of the puncture site on the vessel. Salvage may also be impossible if the puncture is immediately adjacent to the PFA ostium or if anterior plaque prevents SFA cannulation.

It is desirable therefore to provide a device or method that facilitates introduction of a cannula or guidewire into the correct bodily lumen, that avoids or ameliorates at least one of the aforementioned disadvantages or at least provides a useful alternative.

SUMMARY

In accordance with the present disclosure, there is provided an obturator comprising a hollow distal end portion, the distal end portion comprising a distal end and a side hole located proximally of the distal end, the side hole being for receipt of a guidewire and to direct the guidewire laterally from the obturator.

In accordance with the present disclosure there is also provided an obturator comprising a hollow distal end portion, the distal end portion comprising:
  a single lumen;
  a distal end;
  an end hole at the distal end, for receipt of a guidewire extending through the single lumen; and
  a side hole located proximally of the distal end, the side hole being for receipt of a guidewire extending through the single lumen and to direct the guidewire laterally from the obturator, the side hole further being located so that when the obturator is located in a first bodily lumen, in use, a second bodily lumen can be located by flowing contrast medium through the obturator to exit the side hole.

Disclosed herein is a sheath comprising:
  a substantially hollow body having a proximal end, a distal end and a single lumen in the distal end—the single lumen may be for receiving an obturator;
  an end hole at the distal end, for receipt of a guidewire extending through the single lumen; and
  a side hole disposed proximally of the distal end, so that when the sheath is located in a first bodily lumen, in use, a second bodily lumen can be located by flowing contrast medium through the sheath to exit the side hole, the side hole further being for receipt of a guidewire and to direct the guidewire laterally from the sheath.

The end hole and side hole may be accessible from the single lumen.

The distal end portion may comprise an end hole for receipt of the guidewire and being located at the distal end. The end hole may be positioned so that a guidewire extending therethrough extends substantially parallel to a longitudinal axis of the obturator. The end hole may be offset from the longitudinal axis of the obturator.

The side hole may be located on one side of the obturator so that a guidewire extending through the side hole extends at an angle to the obturator.

The distal end portion may taper towards the distal end. The side hole may be located proximally of the taper. The taper may extend from the side hole to this distal end. The taper may instead extend from a location proximal of the side hole, to the distal end.

The side hole may have one of a square, rectangular, triangular shape, circular or elliptical. The side hole may alternatively have a teardrop shape. The teardrop shape may comprise a distally directed apex.

The obturator may further comprise a slit extending between the end hole and side hole.

The obturator may further comprise one or more orientation indicia positioned on a proximal portion of the obturator to indicate a location of the side hole around on a periphery of the obturator.

In accordance with the present disclosure there is further provided a sheath comprising:
 a substantially hollow body having a proximal end and a distal end; and
 a side hole disposed proximally of the distal end,
so that when the sheath is located in a first bodily lumen, in use, a second bodily lumen can be located by flowing contrast medium through the sheath to exit the side hole.

In accordance with the present disclosure there is further provided a sheath assembly comprising:
 a sheath; and
 an obturator as described above.

In accordance with the present disclosure there is further provided a sheath assembly comprising:
 a sheath as described above; and
 an obturator.

In accordance with the present disclosure there is further provided a sheath assembly as described above, wherein the obturator is an obturator as also described above.

The sheath may be a cannula and the obturator is within the sheath or cannula.

In accordance with the present disclosure there is further provided a method for inserting a sheath, comprising threading a sheath assembly as described above onto a guidewire and into a bodily lumen of a subject, the guidewire extending into the side hole of the obturator.

The sheath may be a cannula.

In accordance with the present disclosure there is further provided a method for repositioning a guidewire, comprising:
 threading, onto a guidewire located in a first (e.g. undesired) bodily lumen, a sheath assembly comprising a sheath and an obturator as described above, the guidewire extending through the side hole of the obturator, the side hole being positioned to redirect the guidewire into the second (e.g. desired) bodily lumen.

'General alignment' may be achieved intracorporeally or by withdrawing the assembly, with the wire through its side hole, off a proximal end of the wire (i.e. the end of the wire located extracorporeally), and reinserting the wire through the end hole of the, or a, sheath assembly to thereby generally align the sheath assembly with the desired bodily lumen.

In accordance with the present disclosure there is further provided a method for repositioning a guidewire, comprising:
 threading, onto a guidewire, a sheath assembly comprising a sheath and an obturator as described above, the guidewire extending through the end hole of the obturator and into a subject;
 determining the guidewire and sheath extend into the first bodily lumen of the subject;
 retracting the guidewire into the sheath assembly; and
 advancing the guidewire through the side hole of the sheath assembly and into the second bodily lumen of the subject.

In accordance with the present disclosure there is further provided a method for repositioning a sheath, comprising:
 performing the method described above, for repositioning a guidewire;
 retracting the sheath assembly along the guidewire until the obturator becomes generally aligned with the second bodily lumen; and
 advancing the sheath assembly into the second bodily lumen.

The obturator comprises an end hole, a side hole and a slit extending between the end hole and side hole, and retracting the sheath assembly along the guidewire until the obturator becomes generally aligned with the second bodily lumen may then comprise retracting at least the obturator until the guidewire is captured in the obturator through the slit.

Again, the sheath may be a cannula.

BRIEF DESCRIPTION OF THE DRAWINGS

Some embodiments will now be described by way of non-limiting example only with reference to the accompanying drawings in which:

FIG. 1 comprises FIG. 1a, illustrating cannulation of the PFA, and FIG. 1b illustrating cannulation of the SFA;

FIG. 2 illustrates an obturator—also known as a dilator or introducer—in accordance with present teachings, with guidewires (shown in broken lines) extending from forward (first) and side (second) holes in a distal end portion of the obturator;

FIG. 3 illustrates a cannula assembly with guidewire extending therethrough and a valve attached to an extension tube into a side port of the cannula hub;

FIG. 4 illustrates a distal end region of a cannula assembly in which the distal end portion of the obturator comprises a slit;

FIG. 5, comprising FIGS. 5a and 5b, illustrates two different shapes of side hole;

FIG. 6, comprising FIGS. 6a to 6j, illustrates various configurations of the distal end portion of the obturator;

FIG. 8, comprising

DETAILED DESCRIPTION

Figure 7:
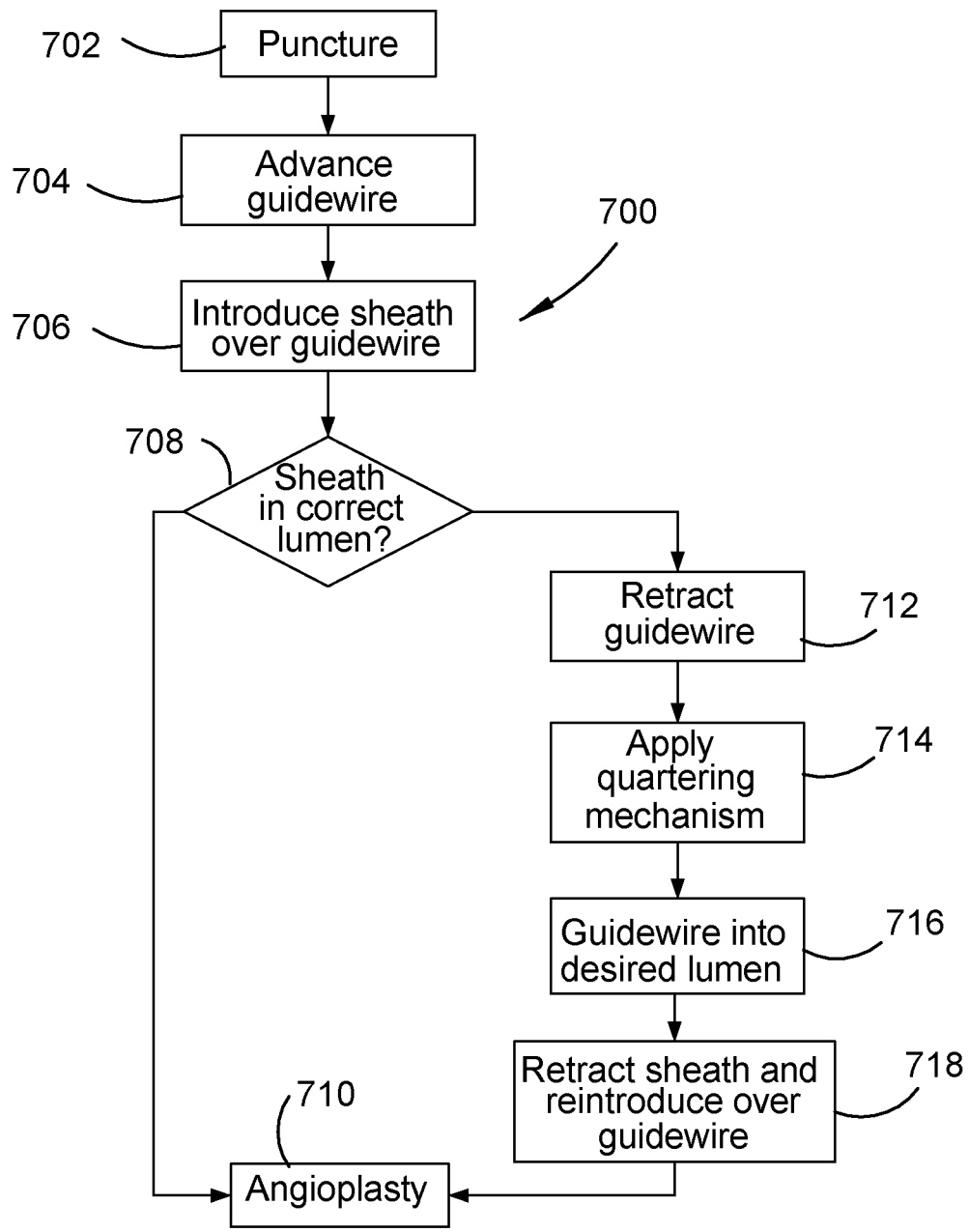
FIG. 7 is a flowchart showing a method for cannulation.

The present disclosures relates to an obturator, a sheath assembly including such an obturator, and methods for use of the sheath assembly. The sheath assembly will hereinafter be described as a cannula assembly for illustration purposes only. It will be appreciated the present obturator may be useable in other assemblies without departing from the teachings herein.

The obturator comprises at least a side hole, and generally two holes—a side hole and an end hole—through which a guidewire can extend. A first of the holes—the end hole—is positioned generally axially with respect to the cannula assembly. For a correctly positioned guidewire, this first hole will be the only hole used since the cannula, tracking or advancing along the guidewire, will follow the guidewire into the correct (i.e. desired) bodily lumen. For an incorrectly placed guidewire, a second of the holes—the side hole—will be used. Advancing the guidewire through the second hole causes it to extend into the desired bodily lumen. The cannula assembly can then be advanced along the guidewire into the desired bodily lumen.

The obturator is intended to improve the ease and speed of salvaging an incorrectly placed guidewire with minimal change or disruption to existing clinical procedural workflows. The obturator may also assist in securing arterial access while minimising inadvertent loss of access during salvage. An advantage of use of the present obturator when salvaging an incorrectly placed guidewire and sheath assembly is that patients and staff are exposed to reduced unnecessary radiation and iodinated contrast.

In general, the present disclosure will be made with reference to the vasculature of a subject (i.e. patient) and vascular lumina of that vasculature. However, it will be appreciated that the present teachings may be similarly applied to other lumina of the body: for example, it may be similarly applied to other bifurcating vessels in the body, beyond the CFA, including both arteries and veins. For example, it could also be used for selective cannulation in the heart, visceral arteries, upper limbs, carotids, brain etc.

FIG. 1 illustrates incorrect placement of a guidewire 108 (FIG. 1a) through a needle 110, followed by correct placement of the guidewire 108 (FIG. 1b) resulting from bouncing the guidewire 108 off the wall 112 of a vascular lumen 108 near an ostium 114. In the arrangement shown in FIG. 1, the various portions of the vasculature 100 are the CFA 102, SFA 104 and PFA 106.

Using the obturator disclosed herein, an interventionist or physician may be able to avoid the uncertainty of correct placement resulting from bouncing the guidewire off the vascular luminal wall and other known techniques. An embodiment 200 of an obturator in accordance with present teachings is shown in FIG. 2. The obturator 200 broadly comprises a hollow distal end portion 202, the distal end portion 202 comprising a first hole 204 and second hole 206 both of which are for receiving a guidewire.

The term "receiving" as used in relation to the guidewire can mean that the hole is threaded over a guidewire that has already been located in the subject, or that the guidewire is advanced through the hole, or another meaning as determined by the context in which the term is used.

The obturator 200 further comprises a hub 208 and grip 210. The hub 208 is for connection to a cannula or other medical device, in a known manner. Similarly, the grip 210 may take any known shape and is for gripping during removal of the obturator 200.

The distal end portion 202 extends from the distal end 212, proximally of the obturator 200. The distal end portion 202 tapers towards the distal end 212. The taper 214 extends from the distal end 212, proximally of the obturator 200. The taper 214 facilitates introduction of the obturator into the subject (not shown).

The distal end 212 is sized to have the same, or slightly larger, diameter as the guidewire during use. The subject's skin may resile to circumferentially contact the guidewire after removal of the needle used to place the guidewire. Close conformance of the distal end 212 of the obturator 200 with the diameter of the guidewire facilitates insertion of the obturator 200 into the pre-existing penetration of the patient's skin.

The second hole 206, which may be interchangeably referred to as a side hole or lateral hole, may be located in the taper 214, or proximally of the taper as shown in FIG. 2. Locating the second hole 206 proximally of the taper 214 means the leading edge of the second hole 206 can direct the guidewire along a lateral trajectory at a greater angle to the longitudinal axis 216 of the obturator 200. In addition, the leading and trailing edges of the second hole 206 are at the same diameter, resulting in a lower likelihood of the second hole 206 catching on the subject's skin during insertion of the obturator 200.

The first hole 204 is located at the distal end 212. The second hole 206 is located proximally of the first hole 204. As used herein, the term "proximally" and similar will refer to being located closer to the end of the obturator, cannula or other medical device, at which the physician or interventionist applies manual control of the medical device. Conversely, "distally" and similar refer to being located further from that end. Thus, the distal end of a medical device is the end of that device that is further from the end to which direct manipulation is applied by the physician or interventionist.

The first hole 204 is positioned so that a guidewire extending therethrough extends substantially parallel to the longitudinal axis 216 of the obturator 200. In some embodiments, the first hole 204 is coaxial, or axially aligned, with the longitudinal axis 216. The first hole is offset from the longitudinal axis 216 of the obturator 200. Since the obturator 200 may be flexible, parallelism and axial alignment may be determined tangentially relative to the distal end 212.

In the present embodiment, the second hole 206 is located on one side of the obturator 200. A guidewire extending through the second hole 206 therefore extends at an angle to the obturator 200. For illustration purposes, FIG. 2 shows guidewires 218, 220 extending from the first hole 204 and second hole 206 respectively, in broken lines as they do not form part of the obturator 200.

The second hole 206 may take any desired shape. For example, the second hole 206 may have a square, rectangular or triangular shape. In the embodiment shown in FIG. 2, the second hole 206 has a rectangular shape (though exact rectangularity is not required to have a "rectangular" shape).

The second hole 206 is located around the periphery of the obturator 200. The second hole 206 therefore extends from a hollow internal lumen of the obturator—such as lumen being known in the art—through the wall of the obturator 200 so that a guidewire can enter a bodily lumen through the second hole.

The obturator 200 of FIG. 2 further comprises one or more, and presently one, orientation indicia 222. The indicium 222 is positioned on a proximal portion of the obturator to assist the physician or interventionist to locate the distal end region in the subject—e.g. in relation to the profunda or SFA. In some embodiments, the indicium may be located towards the distal end of the obturator and be locatable either on fluoroscopy, ultrasound, or by estimation, to provide similar assistance. The indicium 222 indicates a location of the second hole around on the periphery of the obturator. This enables the physician or interventionist to know where the second hole 206 is located relative to the desired bodily lumen. Where more than one side hole is provided, as discussed below, there may be an indicium per side hole.

Figure 9:
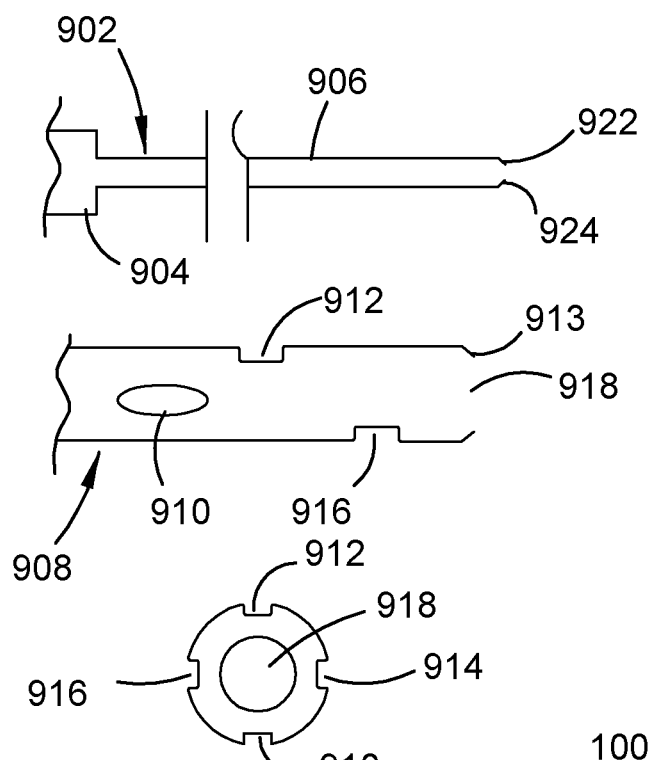
FIG. 9 illustrates longitudinal cross section through the distal end portion of an obturator in accordance with present teachings; a lateral cross section through an alternative obturator in accordance with present teachings; a longitudinal cross section of a vascular sheath or cannula.

FIG. 9a schematically illustrates a longitudinal cross section of an alternative distal end portion 900 of an obturator 908 in accordance with present teachings. In one exemplary embodiment the side hole 910 may have a configuration of an oval shape. The oval shape has a major axis between 2 mm and 15 mm long—e.g. in a longitudinal direction of the hole 910 along the distal end portion 900. The oval shape has a minor axis between 0.33 mm to 3.66 mm long—e.g. in the transverse or lateral direction of the hole 910 along the distal end portion 900. In other embodiments the side hole may be circular, or elliptical either symmetrically or asymmetrically, triangular, square, rectangular or have a teardrop shape.

The obturator may comprise a single side hole as described with reference to FIG. 2. In the present embodiment, the obturator may instead comprise two, three, four or any other number of side holes as required. Presently, the obturator 908 comprises four side holes. The side holes are positioned at different distances from the distal tip 913 so as not to materially weaken the distal end portion 900. The holes are positioned at 12 o'clock (912), 3 o'clock (914), 6 o'clock (910) and 9 o'clock (916) positions respectively, as best shown in FIG. 9b. The holes 910 to 916 are thus spaced equidistantly about the periphery of the distal end portion 900.

FIG. 9b is a view along the longitudinal axis of a transverse cross section of the distal end portion 900 of the obturator 908. The side hole or side holes may be lined with, or have applied strips or shapes of materials of different densities or characteristics that are radiopaque on fluoroscopy, or strengthen various portions of the respective hole to enable proper independent manipulation of the guidewire and obturator during repositioning of each.

To facilitate selective control of the guidewire through each hole 140 to 146, the obturator may comprise a single lumen with quartering mechanism, a dual or triple lumen as desired. Guidewire control and plural lumina are discussed with reference to FIGS. 10 to 17.

FIG. 9c schematically depicts a longitudinal cross section of the proximal and distal ends of a vascular sheath or cannula 902. The cannula 902 comprises, proximally, a haemostasis valve—not shown but well understood in the art—within a hub 904. The hub 904 is located outside of the skin during use and is the portion of a cannula assembly (discussed in more detail with reference to FIG. 3) through which all cannulations commence.

The cannula 902 comprises a lumen 906, and a flushing port (see port 320 of FIG. 3) which enables fluid or contrast to be aspirated or injected down the lumen 906. The obturator 908 is positioned within the lumen 906 during use and the fluid or contrast is often injected through the cannula 902 and obturator 908 into the subject. The fluid or contrast exits either by the longitudinal or first hole 922 and through hole 918 of the obturator 908, through the side hole 910 of the obturator 908, or both.

To facilitate delivery of contrast or fluid, the obturator or obturator insert 908 is hollow in its proximal extremity. The obturator may have either a blind end in its distal extremity or else incorporate a diverting or quartering mechanism (described with reference to FIGS. 10 to 12) to divert the guidewire out the desired side hole upon activation of the diverting or quartering mechanism. The diverting or quartering mechanism facilitates replicable diversion of the path of a guidewire into the desired side hole. In the instance of a blind-ending obturator, initial access will be done using a known obturator with a single end-hole as per normal. Upon discovery of a profunda cannulation the obturator and wire will be removed and the blind-ending obturator with side a side-hole will be inserted into the cannula. The entire cannula-obturator assembly will be retracted until the side-hole aligns with the femoral artery bifurcation. The wire will be advanced down the side-hole into the SFA and passed for a substantial distance. The entire assembly will then be withdrawn over the wire out of the patient, and reintroduced along the guidewire using the, or a, know obturator having an end-hole so that in-line cannulation of the SFA is achieved.

The distance between elements 918 and 910 is between 0.5 to 10 cm. The distance between distal end 924 of sheath 902 is between 3 cm and 20 cm, and preferably 11 cm.

In one embodiment, the sheath 902 may be tapered towards the distal tip or end 924, leading to the exit or longitudinal hole 922, resulting in the hole 922 being considerably narrower than the lumen 906 of the sheath 902. The gauge of the sheath 902 may be suitable for common peripheral vascular interventions, for example between but not limited to 4 Fr and 10 Fr.

FIG. 3 illustrates a cannula assembly 300 comprising a cannula 302 and an obturator 304 as described with reference to FIG. 2. FIG. 3 shows how the hub 306 of the obturator 304 engages with a hub 308 of the cannula 302.

The distal end portion 310 of the obturator 304 protrudes distally of the cannula 302. The distal end portion 310 thereby enters the subject first, widening the penetration formed in the subject and facilitating easier entry of the cannula 302 into the subject.

In this embodiment, the distal end portion 310 protrudes sufficiently that the second hole 312 is located distally of the cannula 308.

The cannula assembly 300 also includes an infusion assembly 314. The infusion assembly 314 comprises a valve 316 and extension tube 318, extending into a side port or infusion port 320 of the cannula hub 302.

The entire complex—i.e. obturator, cannula and other of the cannula assembly—can be made from hypoallergenic, inert, flexible and stretchable materials such as silicone or polymers such as polyurethane.

The obturator 200, 304 of FIGS. 2 and 3 each comprise a distinct and separate first hole and second hole. In contrast, the obturator 400 of FIG. 4, which is received within a cannula 402, comprises a slit 404 extending between the first hole 406 and second hole 408. The relevance of the slit 404 will be explained with reference to FIG. 8.

The cannula 402 of FIG. 4 tapers towards the obturator 400 such that the diameter of the cannula 402 at its distal end is the same as the outer diameter of the obturator 400 when the two are assembled together. In other cases, the cannula 402 may be a sufficiently tight fit around the obturator 400 to substantially avoid catching on tissue of the subject during insertion and use.

The obturators 200, 304 of FIGS. 2 and 3 both included a substantially rectangular side or second hole 206, 312 as shown in FIG. 5a. In other embodiments, the side or second hole 500 may have a teardrop shape as shown in FIG. 5b. The teardrop shape of the side or second hole 500 comprises a distally directed apex 502. Thus, the apex 502 points towards the distal end 504 of the obturator 506. In other alternatives, the apex may be oriented proximally, or is some other desired orientation.

The teardrop shape self-centres the guidewire (not shown) in the second hole 500 when the guidewire extends therethrough. Where a slit is used in conjunction with the teardrop shape, the teardrop shape also facilitates reintroduction of the guidewire into the obturator after repositioning of the guidewire from the undesired lumen of the subject, into the desired lumen. The teardrop shape can permit more gradual bending of the guidewire as it exist the side hole, but may be more difficult to manufacture than a rectangular or other shape side hole.

FIG. 6 shows various embodiments on distal end portions of obturators in accordance with present teachings, each of which is shown extending from a cannula. Each distal end portion tapers towards its respective distal end—e.g. towards the diameter of a guidewire received through the obturator. In some embodiments, however, the distal end portion may be blunt—for example, sized to have the same or similar internal diameter as the outer diameter of a guidewire extending therethrough.

The distal end portions shown in FIGS. 6a to 6c, 6g and 6h each comprise a second tapered region 600. The second hole 602 may be located in the taper described with reference to FIG. 2, in the second tapered region 600 or between the tapered regions as shown.

FIGS. 6a to 6e, 6i and 6j each show rectangular second holes, such a shape being shown in exploded view in FIG. 5a. Similarly, FIGS. 6f to 6h shown teardrop second holes, such a shape being shown in exploded view in FIG. 5b.

FIGS. 6a and 6d to 6f shown the second hole located closer to the distal end of the distal end portion than in FIGS. 6b, 6c and 6g to 6j.

FIGS. 6b, 6d, 6g and 6i each show embodiments where the first and second holes are connected by a slit 604 for return of the guidewire into the obturator lumen (i.e. that which leads to the end hole). As described with reference to FIG. 8, during repositioning of the obturator onto an already repositioned guidewire the slit flexes around the guidewire. The closer the second hole is to the distal end of the obturator, the greater the force that may be applied to the internal wall of the vasculature during repositioning of the obturator. It can therefore be desirable to locate the second hole further proximally in the distal end portion. This would also make it easier to anchor the obturator in the undesired lumen in vivo, while relocating the guidewire.

FIG. 7 shows a flowchart 700 of workflows performed during cannulation. To commence cannulation a puncture is formed in the subject's or patient's skin, and into the vasculature—step 702. In general, the puncture will be a micro-puncture formed by a needle (not shown). A guidewire is then advanced through the needle and into the vasculature—step 704. After step 704, the needle will generally be removed from the guidewire and a sheath (i.e. cannula assembly) threaded onto, or introduced over, the guidewire and into the vasculature—step 706.

The physician then checks whether the cannula assembly is in the correct or desired vascular lumen—step 708. With reference to FIG. 1, this would place the cannula assembly in the SFA. This check can be performed using contrast medium injected into the cannula assembly—e.g. through extension tube 318 of FIG. 3. The contrast medium can be detected using known methods. The check may also be performed manually, by palpation.

If the cannula assembly has entered the desired lumen, then the procedure (e.g. angioplasty) continues—step 710. This will involve removal of the guidewire and obturator from the cannula, and insertion of another device—e.g. a catheter—through the cannula and into the desired vascular lumen.

If it is determined that the cannula assembly has been advanced into the undesired lumen, the guidewire is retracted into the cannula assembly—step 712. The guidewire is retracted until the tip of the guidewire is aligned with, or is proximal of to, the second hole of the obturator.

The guidewire is then advanced through the second hole of the cannula assembly and into a second or desired bodily lumen of the subject—step 714. The guidewire is thus repositioned into the desired bodily lumen.

Relevantly, the cannula assembly used up to, and including, the determination step 708 may be a standard cannula assembly known in the art—i.e. a cannula assembly comprising only a single hole in the obturator, that hole being coaxial with a longitudinal axis of the obturator. Upon determining that the guidewire is in the undesired lumen, that cannula assembly may be removed and unthreaded from the guidewire and a cannula assembly as taught herein then threaded onto the guidewire. Alternatively, a cannula as taught herein may be used from the outset.

In accordance with step 718, the cannula may then be repositioned—e.g. into the desired lumen. This is achieved by retracting the cannula assembly (i.e. sheath) over or along the guidewire. Retraction occurs until the obturator becomes generally aligned with the desired bodily lumen. The term "aligned" in this circumstance means that upon advancing the cannula assembly back along the guidewire, the obturator, and thus the cannula, will be guided into the second, or desired, bodily lumen. The procedure may then continue as usual—step 710.

FIG. 7 thus illustrates the normal or common workflow and a workflow involving repositioning the cannula assembly with minimal disruption to the common workflow. With reference to FIG. 1, the puncture site may be secured by the method 700—i.e. not require a further puncture to be made for repositioning—by having obturator and guidewire operated in a manner that changes the direction of the guidewire while maintaining the sheath inside the PFA. The sheath is only removed from the PFA once the guidewire is safely secured in the SFA. With the guidewire in the SFA, secured by the sheath, the physician or interventionist can now proceed with lower limb angioplasty or some other procedure.

The steps of the workflow 700 involving the cannula assembly described herein, comprising two holes in the obturator (though the obturator may also comprise more than two holes) are mainly involved in steps 712 to 718. It will be appreciated that a procedure may instead comprise two obturators, one in which the distal end portion comprises only a side hole located proximally of the distal end, for directing the guidewire laterally from the obturator, and a separate obturator comprising and end hole.

Figure 8A:
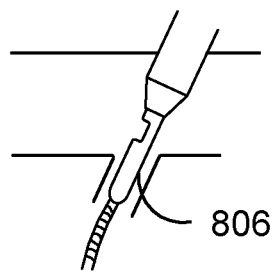
FIGS. 8a to 8j, illustrates steps in the method of FIG. 7.
Figure 8B:
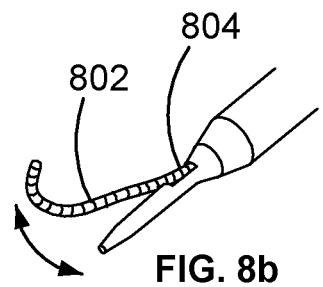
Figure 8C:
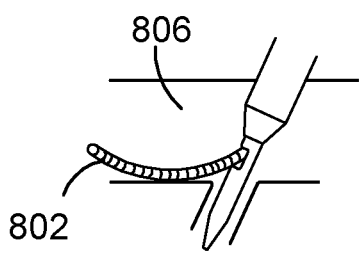
Figure 8D:
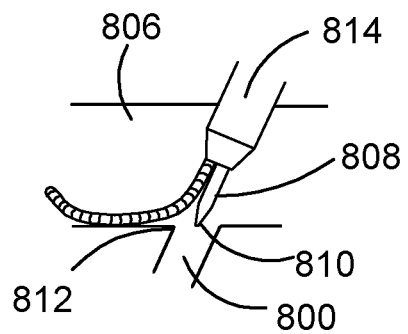
Figure 8E:
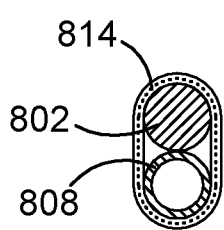
Figure 8F:
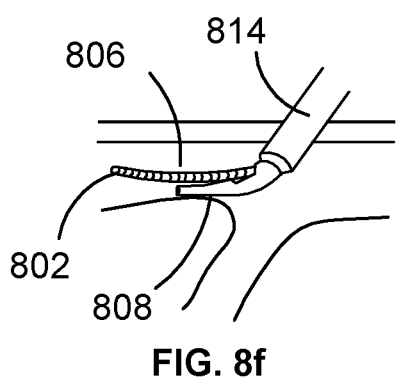

FIG. 8, comprising FIGS. 8a to 8k, illustrates various steps of the workflows of FIG. 7, or states of the sheath assembly during performance of those workflows. FIG. 8a shows a sheath assembly located in the undesired lumen 800 as determined at step 708. FIG. 8b shows the guidewire 802, after retraction and reinsertion or re-advancement along the sheath assembly, extending through the side hole 804. FIG. 8c shows how the guidewire 802 will rest on the desired lumen 806 after advancing through the side hole. FIG. 8d shows the obturator 808 retracted so that its distal end 810 is proximal the ostium 812 between the desired lumen 806 and undesired lumen 800. This retraction step occurs between introduction of the guidewire 802 into the desired lumen 806—steep 716—and retraction of the sheath 814—step 718. In this condition, the obturator 808 and guidewire 802 will be side-by-side in the sheath 814 as shown in FIG. 8e. The obturator 808 and sheath 814 are then advanced back along the guidewire 802 into the desired lumen 806—FIG. 8f.

Figure 8G:
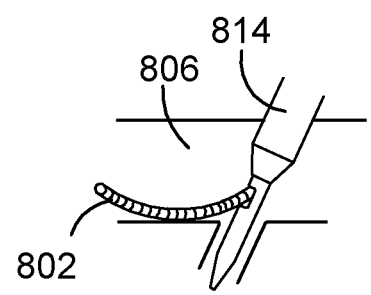
Figure 8H:
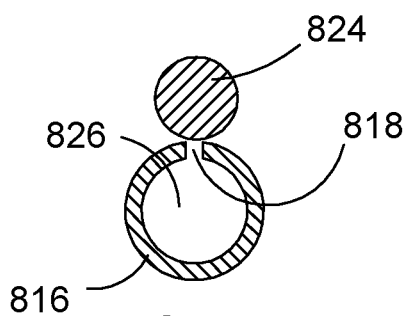
Figure 8I:
Figure 8J:

In an alternative embodiment, the obturator 816 includes a slit 818 between the end hole 820 and side hole 822 as shown in FIG. 8g. After repositioning the guidewire 824 through the side hole 822, the guidewire 824 is located immediately distally of the side hole 822 in the position generally indicated by FIG. 8h. As the obturator 816 is retracted, as shown progressively in FIGS. 8h to 8j, the guidewire 824 flexes the edges of the slit 818 inwardly until the guidewire 824 pushes back into the lumen 826 of the obturator 816. The final position of the obturator 816 during retraction, with the guidewire 824 in the lumen 826, is shown in FIG. 8k. Thus, advancing the obturator 816 will result in it following the trajectory of the guidewire 824 into the desired lumen 828.

With further reference to FIGS. 8c, 8d and 8e, after the guidewire 824 exits the side hole 822 into the second or desired bodily lumen 806, the sheath assembly is retracted along the guidewire 824 until the guidewire 824 and extended distal taper of the obturator 816—i.e. the taper between the side hole 822 and distal end—are wedged within the sheath. In some cases, if the distal taper is long enough, the guidewire 824 will not be recaptured in the obturator 816 at this stage. Instead, the two wedge into the sheath due to the reduce cross section of at the distal taper. This wedging facilitates removal of the obturator 816 out of the sheath assembly while leaving the guidewire 824 in the second or desired bodily lumen 806.

Figure 10:
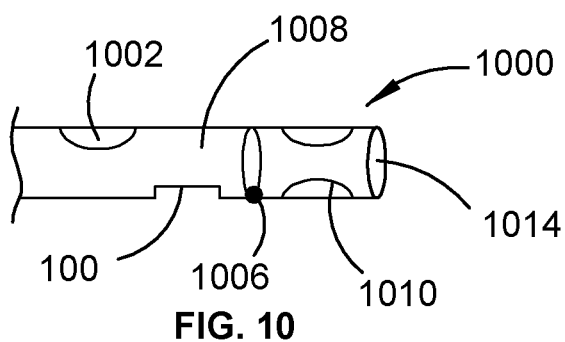
FIGS. 10 to 12 illustrate longitudinal cross sections through a distal end portion of an obturator, comprising a variety of quartering mechanisms.
Figure 11:
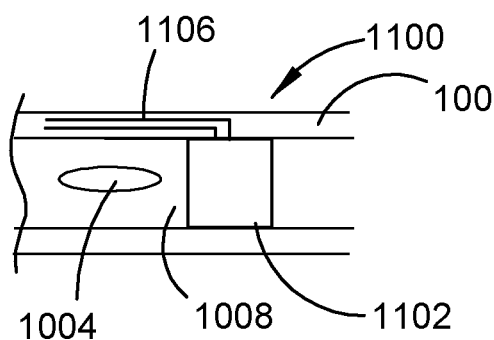
Figure 12:
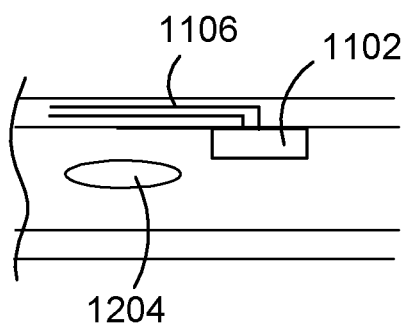

FIGS. 10 to 12 illustrate a variety of quartering systems each comprising a quartering mechanisms and in some cases one or more elements for enabling, aiding and/or facilitating control of the quartering mechanism and thus of the guidewire selectively between end (or first) and side (or second) holes. The quartering system in each case is part of the obturator 1000, 1100. FIG. 10 itself illustrates more than one quartering system. It will be appreciated that, in practice, only a single such quartering system will typically be provided.

In one embodiment, the quartering mechanism is a contoured protrusion 1002. The contoured protrusion is diametrically opposite the side hole 1004 (e.g. if the side hole 1004 is at 6 o'clock then the protrusion 1002 is at 12 o'clock). The protrusion 1002 is relatively proximal to the side hole 1004. The protrusion 1002 preferably slightly overlaps the side hole 1004 such that it deflects the guidewire (not shown) into the side hole 1004.

The shape of the protrusion 1002 may be a symmetrical or asymmetrical hump, or ledge, or wedge. The surface of the protrusion 1002 may be smooth, rough or grooved. The protrusion may be inflatable, e.g. using air or a liquid, through a conduit (not shown) so as to have a collapsed state permitting preferential access of the guidewire through one of the side and end holes—presently the end hole 918 described with reference to FIG. 9a—and an inflated or expanded state directing the guidewire through the other of the side and end holes—presently the side hole 910 as described with reference to FIG. 9a. Expansion and collapse of the protrusion 1002 may be performed in the same manner as expansion and collapse of a balloon catheter in a known manner.

In an alternative embodiment, a flap/leaflet 1006 may be used. The flap 1006 is located distally of the side hole 1004. The flap 1006 can be either oriented to occlude the main lumen 1008, for instance by flipping up (on a hinge, living hinge or otherwise) to force passage of the guidewire through the side hole 1004, or oriented to permit passage of the guidewire down to the distal end of the main lumen 1008. The flap 1006 may take a substantially planar form, may be a ball-valve mechanism rotated between a position in which the hole through the ball of the valve aligns with the main lumen 1008—permitting passage of the guidewire through the ball-valve—and a position in which the hole is out of alignment (e.g. perpendicular to) with the lumen 1008 to prevent access to the distal end. Rotation of the mechanism 1006 may be achieved by control wires and similar, presently used to control implant and removal of medical devices in the vasculature in a known manner. The flap 1006 may instead change elasticity or stiffness to afford greater resistance to passage via an activating mechanism (not shown). The change in elasticity or stiffness may be affected either electrically (e.g. using an elastomer that change properties upon electrical stimulation, such as carbon black filled ethylene-propylene based elastomer (cPBE) embedded in a electrically insulating sheet of polydimethyl siloxane), or mechanically (e.g. by coiling up a very fine helical wire within the flap or inflating the flap body), as will be understood by the skilled person in light of the present teachings.

In yet a further alternative embodiment, an expanding circumferential ring or doughnut 1010 is provided. The expanding ring 1010 can be expanded to occlude the distal lumen upon activation, and thereby force the guidewire through the side hole 1004. Upon activation—e.g. inflation in the same manner as a balloon catheter—the ring 1010 significantly narrows the lumen 1008 to occlude it and preferentially preclude a guidewire from advancing down the lumen 1008—e.g. force the guidewire out the side hole 1004. Similarly, feature 1014 is a ring 1010 is inside the wall 1016 of the sheath. The ring 1014 is constricted upon activation—e.g. by pulling a wire that shortens the circumference of the ring 1014—to occlude the main lumen 1008 and direct the guidewire out the side hole 1004.

FIGS. 11 and 12 show a dirigible device 1102 immediately distal to the side hole 1104. A small channel 1106 is embedded inside the wall 1108 of the sheath (e.g. vascular sheath). The channel connects the dirigible device 1102 to the proximal portion (see hub 308 of FIG. 3) of the sheath. This channel 1106 enables the transport of medium such as fluid or air to the dirigible device to manipulate and adjust its size as seen in FIG. 11 in which it is inflated, and FIG. 12 in which it is deflated. Similar mechanisms can be used for inflation/deflation and control of other mechanisms described with reference to FIG. 10.

In an alternative embodiment, the quartering mechanism for guiding the guidewire to the side hole utilizes an intraluminal inflatable or bag that is meant to act as a dirigible device as discussed with reference to FIGS. 11 and 12. This dirigible apparatus is connected to the outside via a channel embedded inside the wall of the vascular sheath and can be activated via the injection of medium such as saline, contrast or gas such as carbon dioxide.

Upon activation, this dirigible device will expand and occlude the lumen of the vascular sheath completely. Additionally, the expansion may also stretch the sheath in the immediate vicinity and secondarily expand the width of the side hole to facilitate the guidewire tip cannulating this newly enlarged opening. In addition, if the main lumen is completely occluded, contrast can be flushed via the side hole to visualize the ostium of the profunda or undesired lumen.

It will be appreciated that the location of the quartering mechanisms and other elements of the quartering systems shown in FIGS. 1 to 12 may not be exactly as shown in relation to the side hole 1004, 1104, 1204. However, placement of those quartering mechanisms to achieve the purpose of directing the guidewire through the side hole 1004, 1104, 1204 will be clear to the skilled person in light of the present teachings.

Figure 13:
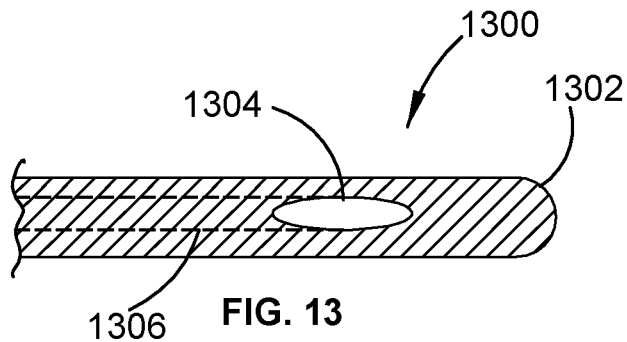
FIG. 13 illustrates a longitudinal cross section through a distal end portion of an obturator.

One or more obturators may instead be used as part of the quartering system. With reference to FIG. 13, the distal end 1300 of an obturator 1302 is designed to fit snugly inside the lumen of the vascular sheath—see, e.g. FIG. 9. The tip of the obturator 1302 maybe tapered or bullet shaped to facilitate puncturing of the arterial wall, during entry into the vasculature, or the wall of another bodily lumen as required. In some embodiments the obturators may have a slightly larger gauge than the sheath and upon entering the lumen of the sheath may dilate and stretch the wall of the sheath.

The obturator 1302 comprises a lumen 1306 having a side hole 1304, with the distal end 1300 being blind. In some cases, an obturator having only and end hole—e.g. a traditional obturator—may be used until it is determined that the obturator has entered an incorrect bodily lumen. That obturator may then be removed and obturator 1302 threaded onto the guidewire. The intention of using obturator 1302 is to shift the end of the guidewire into the desired bodily lumen. The cannula assembly can then be advanced along the correctly placed guidewire.

The side hole 1304 may be oval, elliptical, quadrilateral or otherwise.

Figure 14A:
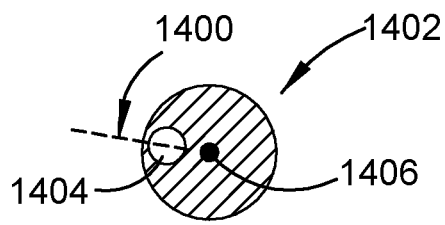
FIGS. 14a and 14b illustrate end and longitudinal cross sectional views of a distal end portion of an alternative obturator.
Figure 14B:
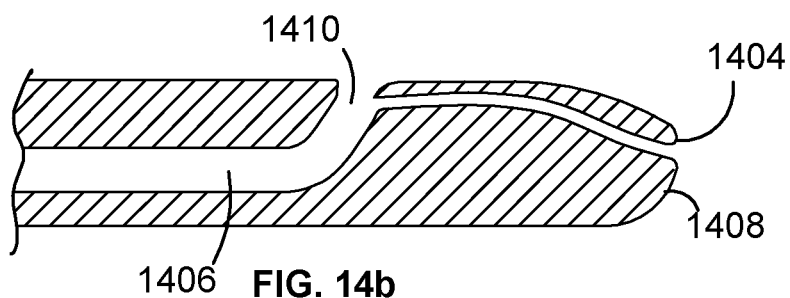

In an alternative embodiment shown in FIG. 14*a*, the side hole 1400 may be in alignment with the end hole 1404 of the obturator 1402, off the main internal lumen 1406 as shown in FIG. 14*b*. While the end hole is not strictly at the very distal end of the obturator, it is forward facing with respect to the longitudinal axis of the obturator and will be referred to herein as an end hole. Also, alignment of the end hole and side hole refers to both being located in generally the same plane defined by the longitudinal axis of the obturator and a radial line normal to the longitudinal axis. Moreover, both the side and end hole are to one side of the longitudinal axis. The main internal lumen 1406 may come out at or near the edge of the distal end 1408, offset from the midline as shown in FIGS. 14*a* and 14*b*. A quartering mechanism described with reference to FIGS. 10 and 11 may be used to direct the guidewire between hole 1404 and hole 1400.

In FIG. 14*b*, the proximal lumen is at 12 o'clock and the distal lumen is central.

Figure 15A:
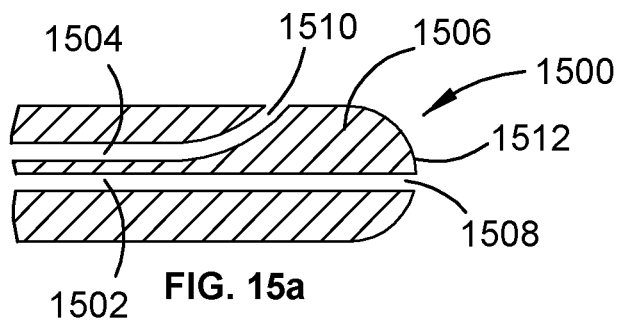
FIGS. 15a, 15b and 16 illustrate longitudinal cross sections through a distal end portion of an obturator comprising multiple lumina.
Figure 15B:
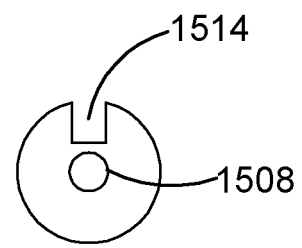

FIG. 15*a* illustrates an embodiment of on obturator 1500, particularly the distal end portion 1506, comprising two separate lumina 1502, 1504. The lumina 1502, 1504 can be cannulated individually. For example, initially (e.g. at step 706) the sheath will be threaded over the guidewire with the guidewire extending into end hole 1508. Once it is determined that the guidewire has been incorrectly positioned in the undesired bodily lumen, then the obturator 1500 is retracted while leaving the cannula or sheath in position. The obturator 1500 is removed from the guidewire and re-threaded back onto the guidewire with the guidewire extending through the side hole 1510. When the obturator 1500 emerges through the distal end of the sheath, with the side hole 1510 oriented towards the desired bodily lumen, the guidewire will be flexed back out of the undesired bodily lumen into the desired bodily lumen. The sheath assembly can then be advanced into the desired bodily lumen.

For this to be achieved, there will generally be some flex or spare space within the sheath to permit that portion of the obturator between the side hole 1510 and tip 1512 to progress through the sheath next to the guidewire. Alternatively, a groove 1514 (see FIG. 15*b*) may be incorporated into the portion of the obturator, in which the guidewire is received during advancement of the obturator 1500 along the sheath.

One lumen 1504 is shorter than the other 1502, and exits side hole 1510 whereas the other lumen 1502 is longer and exits centrally at hole 1512 at the distal end 1512 of the obturator 1500.

Figure 16:
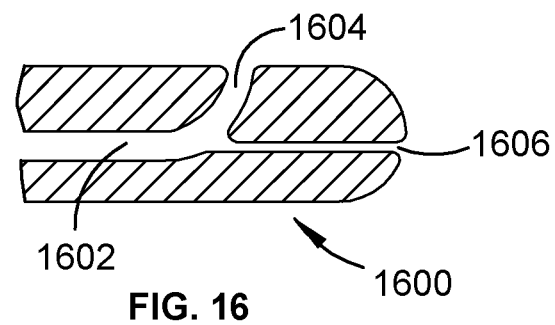

FIG. 16 describes an obturator 1600 with a diverting lumen 1602 to attain side hole 1604 cannulation of the bodily lumen as before, with the difference that the distal lumen continues with an abrupt taper to end hole 1606. This results in straight cannulation only being possible with a fine wire (eg 0.018" or 0.014"). End hole 1606 has a smaller diameter than side hole 1604. Thus, standard wires (ie 0.035") will be diverted out the side hole 164. This would allow preservation of wire access in the PFA while simultaneously enabling preferential cannulation into the SFA. It will be appreciated that a similar arrangement could allow preferential straight cannulation, by providing an end hole with a larger diameter than the side hole. A correspondingly larger diameter lumen will need to extend to the end hole, than the diameter of the lumen extending to the side hole, from the main lumen. Moreover, the internal lumen of the obturator may permit simultaneous positioning of a fine guidewire into the smaller diameter hole, and of a larger guidewire through the larger diameter hole. In addition, even where the holes are the same size or otherwise, the positioning of a guidewire in one hole may force a second guidewire to exit the other hole.

Figure 18:
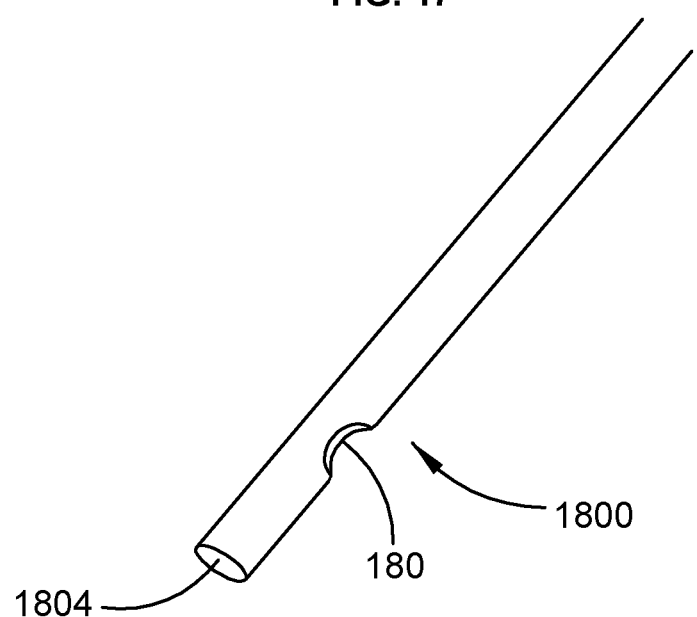
FIG. 18 illustrates a sheath or cannula in accordance with present teachings.

The present disclosure, particularly FIG. 18, also discloses a sheath 1800. The sheath 1800 comprises a side hole 1802 and a distal end 1804. In use, if an obturator (whether as taught herein or known), with the guidewire threaded through its end hole, is used with sheath 1800 and it is determined the sheath is in the undesired lumen, the obturator can be removed. Contrast medium is then flowed (e.g. injected) through the sheath 1800. The contrast medium will exit the distal end 1804 if that end 1804 is open. The contrast medium will not exit the distal end 1804 if the distal end is blind (i.e. closed). In both cases, contrast medium will exit the side hole 1804. The sheath 1800 can then be moved, if necessary, until the side hole 1804 is aligned with the desired lumen as indicated by contrast medium flowing out the side hole into the desired lumen, the contrast medium being visualised in a known manner. The guidewire can then be removed, an obturator as taught herein inserted, and the guidewire threaded so that its side hole aligns with the side hole 1804 of the sheath—e.g. as determined when the hub of the obturator meets the hub of the sheath, or by providing indicia on one or both of the obturator and sheath to indicate the relative alignment of the side holes. The guidewire is then threaded through the side hole of the obturator to project from the side hole of the sheath 1800 into the desired lumen. The sheath assembly may then be withdrawn and to relocate the sheath and/or sheath assembly on the guidewire such that the guidewire projects distally of the sheath 1800, which can then be advanced into the desired lumen. The sheath 1800 may be a cannula or cannulation catheter, or other medical device.

Figure 17:
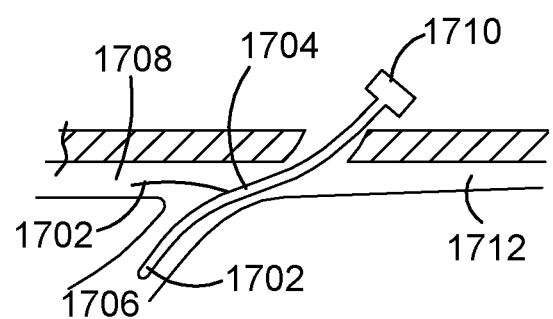
FIG. 17 illustrates a sheath assembly in accordance with present teachings, introduced into an undesired bodily lumen, with a guidewire extending through the side hole into the desired bodily lumen.

FIG. 17 illustrates how the obturator will be positioned in situ with the distal end 1700 within the profunda or PFA 1706, and the guidewire 1702 within the SFA 1708 after cannulating the side hole 1704. For illustration purposes, the hub 1710, CFA 1712 and cannula 1714 are also shown.

The obturators, sheath/cannula assemblies described herein enable easy cannulation of the "side hole" on the obturator by engaging the guidewire and diverting its direction from within the vascular sheath to exit more proximally the body of the obturator at an angle to the obturator. The guidewire is thereby intended to pass distally down the SFA.

In some embodiments, a combination of a vascular sheath and a hollow shafted but blind-ending obturator can be used, the obturator having a side exit a distance away from the blind end. Of note, the side hole on the obturator is equal or larger than the dimension of the side holes on the sheath. The blind-ending obturator shaft may be made of materials that are stiffer and may be of a diameter slightly larger than that of the vascular sheath to allow the obturator to dilate and stretch the outer sheath when the obturator is inserted inside the sheath.

This is depicted in FIG. 17 in which the side hole of the obturator and the side hole of the sheath are orientated and aligned by, for example, using one or more indicia such as external markings, or radiopaque markings visible on x-ray. In some other embodiments, haptic feedback can be used—e.g. a "click" and partial lock/grip when the obturator is aligned with the cannula. In this preferred embodiment, the side hole on the sheath may be about 3 to 6 cm from the distal tip. The obturator with the blind ending tip is slightly longer than the length of the vascular sheath between the proximal hub and the furthest side hole. In a variation of this embodiment, the obturator may have a smaller distal channel or lumen to enable introduction of the obturator through the sheath over an existing fine wire located within the PFA, such that the SFA can be preferentially cannulated through the side hole using a larger wire—e.g. two wires may be within the obturator, one fine wire extending distally from the end hole and the other, larger wire extending laterally from the side hole—see FIGS. 14 and 16.

The perceived workflow for use of said obturator would be, in the case of the blind-ending obturator for the wire to be removed leaving the sheath in the PFA:

insertion of the obturator—e.g. so that its tip extends to within the PFA;

localisation of the bifurcation between the desired and undesired lumina—e.g. PFA/SFA—using contrast injection, with slow withdrawal of the entire assembly until the correct level is reached as indicated by contrast flowing into the desired lumen (this step can be incorporate into the method of FIG. 7); and rotation of the sheath assembly until the side hole(s) align with the desired lumen—e.g. align with the PFA ostium—with or without final confirmatory angiographic runs to prove alignment before cannulation.

In the case of a fine-hollow obturator the existing wire would be changed to a 0.018" or smaller wire to maintain access in the undesired lumen—e.g. the PFA—and the obturator advanced or railed over the wire to end in the desired lumen—e.g. the SFA—as before. The remainder of the workflow would remain the same. Insertion of a second wire would now cause diversion down the side hole.

In an alternative embodiment, the side hole may incorporate a mechanism for detection of the edge of the puncture, for instance by flashback, or cessation thereof, of blood up a suction channel, or else by injection of contrast down an injectable channel, which may allow for activation of a separate mechanism for suture or otherwise closure of the puncture site, not described here.

It is envisioned that contrast will be flushed through either both the distal end and side holes, or else preferentially through one or the other, to demonstrate that the side hole is sitting proximal to the bifurcation of CFA into SFA and PFA—i.e. the bifurcation between the desired and undesired lumina—and in position for wiring. It is also envisioned that radiopaque markers on the side of the sheath will enable the operator to easily align the side hole with the opening of the undesired lumen by rotating the sheath until the marker is in the appropriate position.

It is further envisioned that, in some embodiments, the sheath will be withdrawn over the guidewire, now extending into the desired lumen, in its side hole and reintroduced via the wire in its main, working or longitudinal central lumen so that work may continue down the desired lumen and more distally.

It is conceived that this concept may be utilized for retrograde punctures and may facilitate the easy cannulation of the internal iliac artery, the crossing of the aortic bifurcation, the cannulation of visceral branches during procedures that require retrograde access, or other bodily lumina. The principles will remain the same although the sizes will likely range up to 24 F or larger, and the lengths of the sheath and obturator may increase to 15 cm or even longer as needed for a particular application, without departing from the teachings herein.

In this specification and the claims that follow, unless stated otherwise, the word "comprise" and its variations, such as "comprises" and "comprising", imply the inclusion of a stated integer, step, or group of integers or steps, but not the exclusion of any other integer or step or group of integers or steps.

The various embodiments and variations thereof illustrated in the accompanying Figures and/or described herein are merely exemplary and are not intended to limit the scope of the invention. It is to be appreciated that numerous variations of the invention have been contemplated as would be obvious to one of ordinary skill in the art with the benefits of this disclosure. Rather, the scope and breadth afforded this document should only be limited by the claims provided herein while applying either the plain meaning to each of the terms and phrases in the claims or the meaning clearly and unambiguously provided in this application.

References in this specification to any prior publication, information derived from any said prior publication, or any known matter are not and should not be taken as an acknowledgement, admission or suggestion that said prior publication, or any information derived from this prior publication or known matter forms part of the common general knowledge in the field of endeavour to which the specification relates.

The invention claimed is:

1. An obturator comprising a hollow distal end portion, the distal end portion comprising:
    a single lumen;
    a distal end;
    an end hole at the distal end, for receipt of a guidewire extending through the single lumen; and a side hole located proximally to the distal end, the side hole being for receipt of the guidewire extending through the single lumen, from a position proximal to the side hole, and to direct the guidewire laterally from the obturator, the side hole further being located so that when the obturator is located in a first bodily lumen, in use, a second bodily lumen can be located by flowing contrast medium through the obturator to exit the side hole, the obturator further comprises a flexible slit extending between the end hole and side hole configured to flex around the guidewire to allow the guidewire to be received into the single lumen as the obturator is retracted.

2. An obturator according to claim 1, wherein the end hole is offset from the longitudinal axis of the obturator.

3. An obturator according to claim 1, wherein the distal end portion tapers towards the distal end.

4. An obturator according to claim 3, wherein the side hole is located proximally of the taper.

5. An obturator according to claim 1, further comprising one or more orientation indicia positioned on a proximal portion of the obturator to indicate a location of the side hole around on a periphery of the obturator.

6. A sheath assembly comprising:
an obturator according to claim 1; and
a sheath surrounding the obturator, the sheath comprising:
a substantially hollow body having a proximal end, a distal end and a single lumen in the distal end for receiving an obturator;
an end hole at the distal end, for receipt of a guidewire extending through the single lumen; and
a side hole disposed proximally of the distal end, so that when the sheath is located in a first bodily lumen, in use, a second bodily lumen can be located by flowing contrast medium through the sheath to exit the side hole, the side hole further being for receipt of a guidewire and to direct the guidewire laterally from the sheath.

7. A sheath assembly according to claim 6, wherein the obturator is arranged within the sheath to selectively access the end hole and side hole from the single lumen.

8. A sheath assembly according to claim 6, wherein the sheath is a cannula.

9. The obturator according to claim 1, wherein the side hole has a teardrop shape, having a distally directed apex.

10. The obturator according to claim 1, wherein the slit is configured to flex around the guidewire to allow the guidewire to be received into the single lumen as the obturator is retracted, so that the guidewire does not extend through the side hole.

* * * * *